US00PP12424P2

(12) United States Plant Patent
Lamb

(10) Patent No.: US PP12,424 P2
(45) Date of Patent: Feb. 26, 2002

(54) ANTHURIUM PLANT NAMED 'PURPLE PLUM'

(75) Inventor: Ann E. Lamb, Sebring, FL (US)

(73) Assignee: Twyford Plant Laboratories, Inc., Sebring, FL (US)

( * ) Notice: Subject to any disclaimer, the term of this patent is extended or adjusted under 35 U.S.C. 154(b) by 0 days.

(21) Appl. No.: 09/549,534

(22) Filed: Apr. 14, 2000

(51) Int. Cl.[7] ..... A01H 5/00
(52) U.S. Cl. ..... Plt./368
(58) Field of Search ..... Plt./365, 368, 367, Plt./369

(56) References Cited

U.S. PATENT DOCUMENTS

PP7,441 P * 2/1991 Tagami ..... Plt./369
PP11,159 P * 12/1999 Hodell ..... Plt./368

* cited by examiner

*Primary Examiner*—Bruce R. Campell
*Assistant Examiner*—Kent L. Bell
(74) *Attorney, Agent, or Firm*—Foley & Lardner

(57) ABSTRACT

A new Anthurium plant named 'Purple Plum' particularly distinguished by its abundant, small, purple spathes which are clustered in the center of the plant and held high above the foliage. The foliage is medium-green and moderately glossy. Plants of 'Purple Plum' are short in stature, but well-branched, and best suited for cultivation in 15-cm pots.

2 Drawing Sheets

BACKGROUND OF THE INVENTION

The present invention comprises a new and distinct cultivar of Anthurium plant, botanically known as *Anthurium× hybrid*, and hereinafter referred to by the cultivar name 'Purple Plum'.

The new cultivar is a product of a planned breeding program, and was obtained from a cross made during such a program in Florida, in March of 1993. The female or seed parent was the patented cultivar *Anthurium andraeanum* 'Pink Aristocrat' (U.S. Plant Pat. No. 7,441). The male or pollen parent was an unnamed proprietary *Anthurium× hybrid* seedling identified by number code 'No. 167', maintained by the inventor, and used only for breeding purposes.

'Purple Plum' was discovered and selected as a flowering plant within the progeny of the stated cross by the inventor, Ann E. Lamb, in November 1995 in a controlled environment in Florida.

Asexual reproduction of the new cultivar performed by the inventor by division done in Apopka, Fla., and tissue culture done in Sebring, Fla., was used to increase the number of plants for evaluation and has demonstrated that the combination of characteristics as herein disclosed for the new cultivar are firmly fixed and retained through successive generations of asexual reproduction and reproduces true to type.

BRIEF DESCRIPTION OF THE INVENTION

The following traits have been repeatedly observed and are determined to be basic characteristics of 'Purple Plum' which in combination distinguish this Anthurium as a new and distinct cultivar:

1. Plants produce many small, purple, cordate spathes each with a dark-purple spadix;

2. Spathes are held high above the foliage in the center of the plant;

3. Plants bloom abundantly, often having five or more inflorescences open at one time;

4. Foliage is medium-green and moderately glossy;

5. Plants have many basal branches; and

6. Plants are short in stature and are best suited for production in 15-cm pots.

'Purple Plum' has not been observed under all possible environmental conditions. The phenotype of the new cultivar may vary significantly with variations in environment such as temperature, light intensity, and daylength, without any change in genotype.

In comparison to the female parent plant, 'Pink Aristocrat', the spathes of 'Purple Plum' are smaller, more numerous and purple in color. 'Purple Plum' is shorter and more highly branched than 'Pink Aristocrat'. The leaves of 'Purple Plum' are smaller and more numerous than those of 'Pink Aristocrat'. In addition, 'Purple Plum' is more tolerant of adverse growing conditions than is 'Pink Aristocrat'.

In comparison to the male parent plant, 'No. 167', the spathes of 'Purple Plum' are more numerous, purple in color, and held upright above the foliage on tall, straight peduncles. The spathes of 'No. 167' are pink to pale lavender in color, and are carried among or just above the foliage, on curved, flexible peduncles. The leaves of 'Purple Plum' are smaller, more numerous, and not as shiny as those of 'No. 167'. 'Purple Plum' grows considerably faster than 'No. 167'.

Of the commercial cultivars known to the present inventor, the most similar in comparison to 'Purple Plum' is the cultivar Anthurium×hybrid 'Lavender Aristocrat' (U.S. Plant Pat. No. 9,449). In comparison to 'Lavender Aristocrat', the spathes of 'Purple Plum' are smaller and are more numerous. Plants of 'Purple Plum' are shorter and produce more basal branches than plants 'Lavender Aristocrat'. The leaves of 'Purple Plum' are smaller and more numerous than those of 'Lavender Aristocrat'. Plants of 'Purple Plum' are more tolerant of adverse growing conditions than plants of 'Lavender Aristocrat'.

BRIEF DESCRIPTION OF THE DRAWING

The accompanying color photographic illustrations shows typical characteristics of 'Purple Plum', with colors being as nearly true as possible with illustrations of this type.

DETAILED BOTANICAL DESCRIPTION

Figure 1:
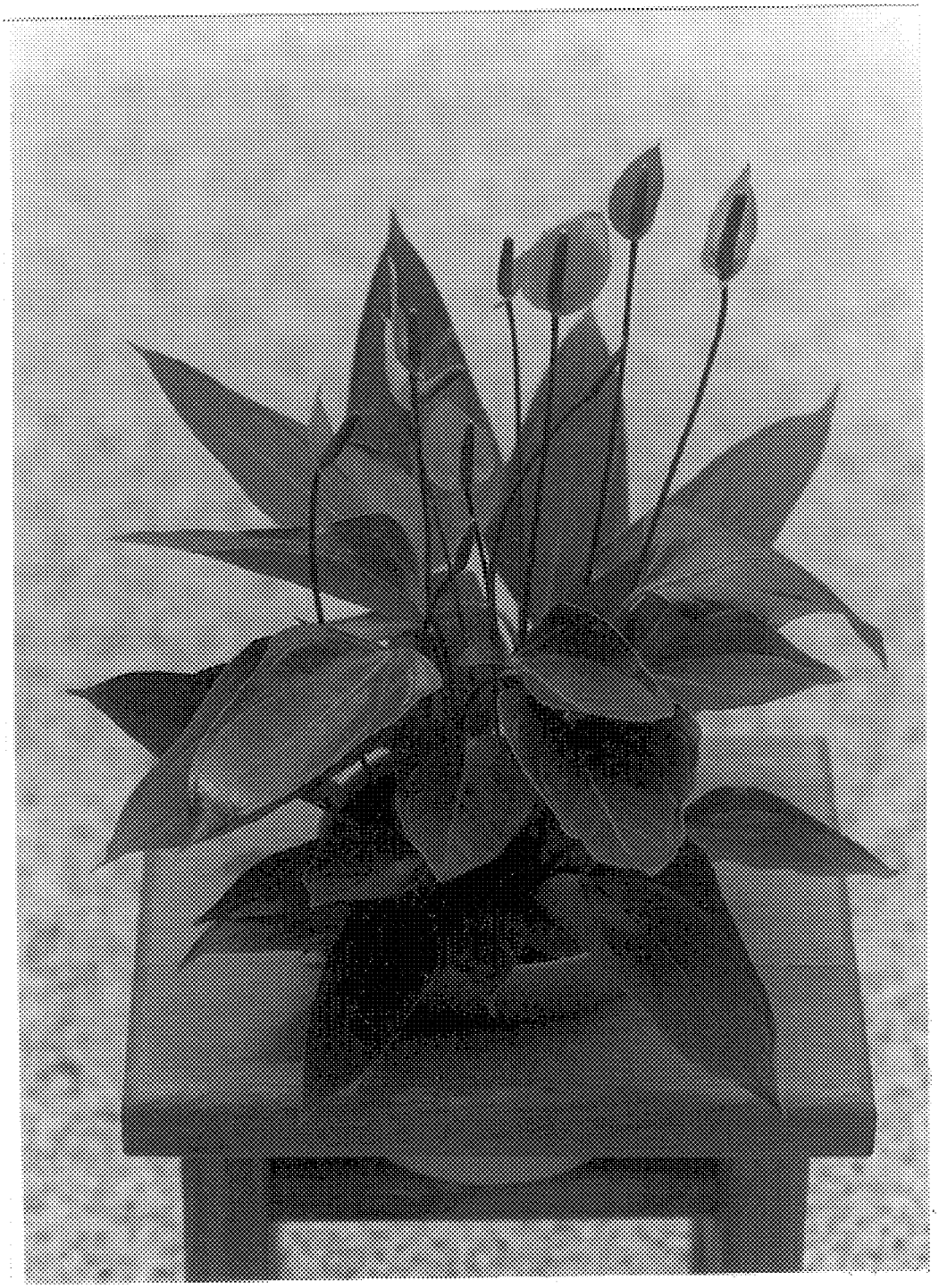
FIG. 1 illustrates a view of the inflorescence and foliage of a one year old plant of 'Purple Plum' in a 15 cm pot.
Figure 2:
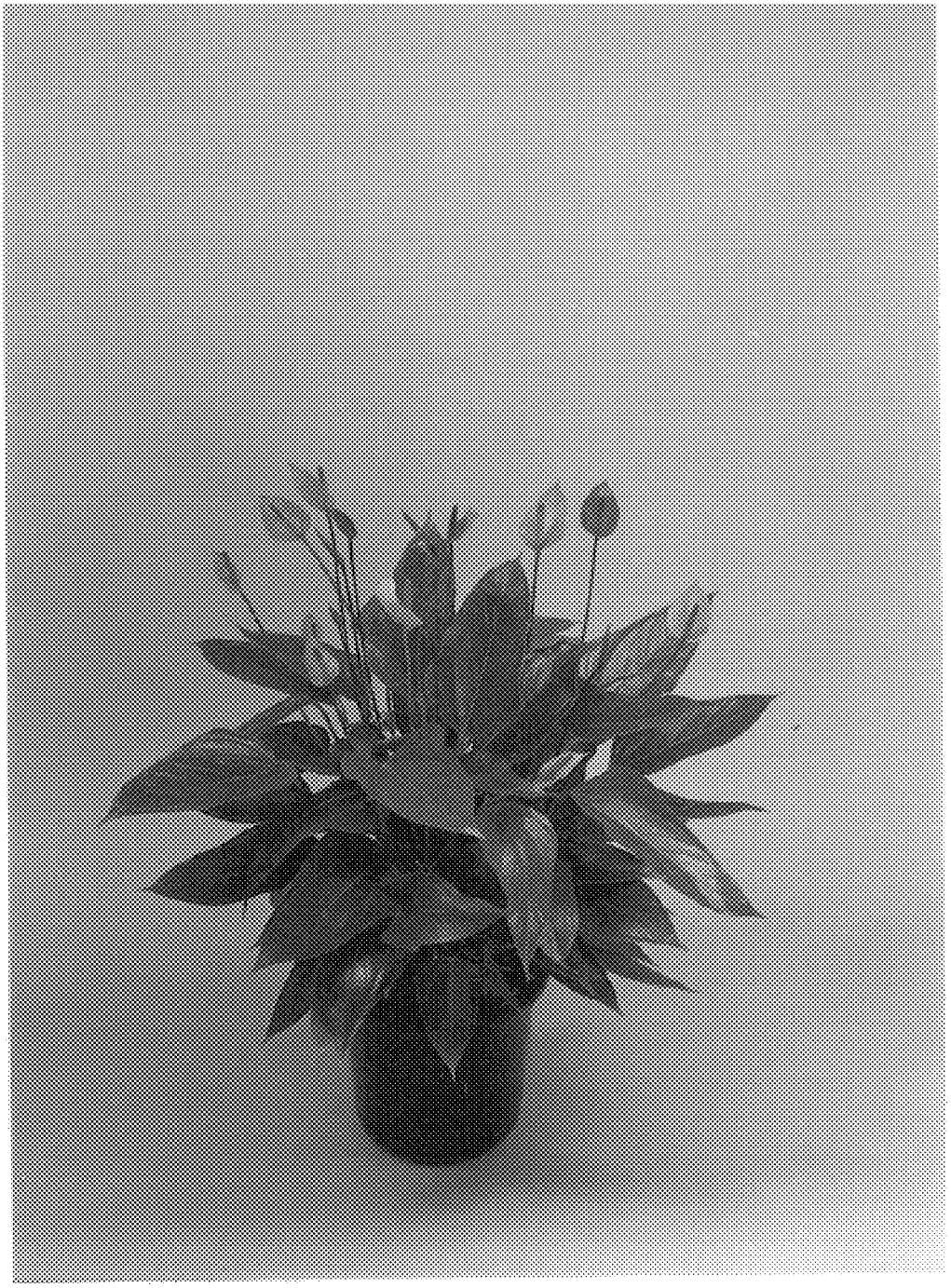
FIG. 2 illustrates a full view of a 1½ year old plant of 'Purple Plum' in a 20 cm pot.

The following observations, measurements and values describe 12 month old plants grown in Homestead, Fla. under shade house conditions typical of the horticultural industry in South Florida. All color references are measured against The Royal Horticultural Society (R.H.S.) Colour Chart. Colors are approximate as color depends on horticultural practices such as light level and fertilization rate, among others, without, however, any variance in genotype.

Classification:

*Commercial.*—*Anthurium×hybrid* cv. 'Purple Plum'.

Parentage:

*Male parent.*—Unnamed, proprietary *Anthurium×hybrid* seedling, 'No. 167'.

*Female parent.*—Anthurium andraeanum 'Pink Aristocrat'.

Propagation: Vegetative, by tissue culture.

Plant: Under appropriate growing conditions, plant reaches a size of approximately 23 cm to 25 cm in height, measured from the soil surface to the top of the leaf canopy,and approximately 38 cm to 41 cm in width, after approximately 7 months. The plant has approximately 6 basal branches.

Leaves:

*Form.*—The leaf blade is ovate with a cuspidate tip and a truncate to slightly cordate base. The margins are entire. The midrib is straight over the length of the leaf. The leaf margins are straight or slightly wavy. The leaf blade is rigid and leathery in texture with a moderately glossy upper leaf surface.

*Size.*—Leaf blades of a flowering-sized plant are approximately 15 cm to 16.5 cm in overall length and approximately 8 cm to 9.2 cm in width when measured at the widest point.

*Veins.*—The veins are sunken. The leaf blade is flat or slightly convex between veins on the upper surface. The midrib protrudes from the upper surface of the leaf for approximately ⅔ the length of the leaf. Well defined primary veins radiate out from the juncture of the petiole and the leaf. Veins stand out prominently on the lower side. The midrib is keeled on the lower leaf surface. There are approximately 6 primary veins on the leaf.

*Petiole.*—The petiole is approximately 12.5 cm to 13.7 cm in length from the base of the petiole to the base of the leaf blade on the primary shoot. The petiole is approximately 3.7 mm in diameter just below the geniculum. The portion of the petiole below the geniculum is straight.

*Petiole sheath.*—The petiole sheath is approximately 2.1 cm in length and approximately 4 mm in width at the midpoint. The tip of the petiole sheath is bluntly rounded. The margin has several folds and undulations. There is approximately 8.2 cm to 8.9 cm between the top of the petiole sheath and the base of the geniculum.

*Geniculum.*—The geniculum is approximately 1.7 cm in length, approximately 4.5 mm in diameter, and is often curved. There is no space between the top of the geniculum and the base of the leaf blade. The color varies between RHS 146B and RHS 146C.

*Lobes.*—The leaf has two rounded lobes which do not extend past the petiole leaf junction. The distance from the petiole/leaf juncture to the highest point on the lobes is approximately 5.0 cm to 5.5 cm.

*Colors.*—Leaf: Upper surface: Darker and greener than, but closest to, RHS 137A. Lower surface: RHS 146C. Midrib: Upper surface: RHS 146C. Lower surface: RHS 146D. Petiole: Varies between RHS 146B and RHS 146C. Petiole sheath:RHS 146C.

Inflorescence:

*Immature.*—The spathe is tightly rolled around the spadix and emerges from the petiole sheath. The spathe is fully open approximately when the peduncle is fully elongated, approximately 35 cm to 40 cm above the soil surface. The color of the flower peduncle varies between RHS 146A and 146 B, tinged with RHS 166A on surfaces exposed to bright light.

*Mature.*—Spathe color: Fully open: Upper surface: Color varies between RHS 186A and RHS 186B. Lower surface: Color varies between RHS 186B and RHS 186C. Faded: Upper surface: RHS 158B flushed with purple, color varying between RHS 186C and RHS 186D. Lower surface: RHS 158B tinged with purple, color varying between RHS 186C and 186D with occasional speckles of RHS 146C. Apex: Both surfaces tinged with RHS 146C.

*Arrangement.*—The inflorescence terminates as a straight wiry peduncle and opens vertically above the leaves.

*Shape.*—The spathe is ovate with a cordate to truncate base and a cuspidate tip. It is cupped when first open, flattening with age. The spathes typically do not reflex.

*Size.*—The fully expanded spathe is approximately 4.4 cm to 5.9 cm long and approximately 3.2 cm to 4.3 cm in width (Spathe not flattened for measurement).

*Flowering time.*—After approximately 7 months from a 20-week-old liner, for an untreated plant as illustrated in sheet 1, depending on season, approximately 9 open blossoms and 3 buds may be present. Smaller blooms may occur on less mature growth. First flowers are typically produced approximately 4–5 months after planting a 20-week-old liner. Approximately 1–3 flowers are present.

*Lastingness of the individual inflorescence.*—4–6 weeks on the plant, 2 weeks if cut and placed in water.

Fragrance: Slight, mint tinged with eucalyptus, most noticeable in the morning.

REPRODUCTIVE ORGANS

Spadix:

*Flower amount.*—Approximately 50–80 flowers per spadix, depending on spadix size.

*Size.*—Approximately 2.9 cm to 4.0 cm in height and approximately 7 mm in width.

*Color.*—When the spathe unrolls, the spadix is RHS 186C at the base, becoming RHS 79A at the apex. The spadix becomes RHS 84C (base) and RHS 83D (tip) with age.

*Stamens.*—Anthers and filaments are minute and not clearly visible. Pollen is white in color.

*Pistil.*—Translucent white, protruding between the staminate flowers, firmly fixed to the main axil. The pistils extend approximately 0.5 mm beyond the stamens. 1 pistil per flower.

Fruit: Length 6 mm, width 4 mm, elliptic, berry. Color is yellow/orange RHS 20C, tinged with green 147C when ripe. Flesh of fruit is translucent yellow-orange RHS 22B, sticky.

Seed: Elliptic, 3.5 mm long, 2 mm wide, color RHS 147 B.

Roots: White fleshy roots with fine laterals.

Pest/disease susceptibility/resistance: No resistance/susceptibility observed to date.

I claim:

1. A new and distinct cultivar of Anthurium plant named 'Purple Plum', as illustrated and described.

* * * * *